(12) United States Patent
Choudhary et al.

(10) Patent No.: US 10,765,716 B2
(45) Date of Patent: Sep. 8, 2020

(54) OBESITY TREATMENT

(71) Applicants: Muhammad Iqbal Choudhary, Karachi (PK); Sammer Yousuf, Karachi (PK); Misha Siddiqui, Karachi (PK); Madiha Mukhtar, Karachi (PK)

(72) Inventors: Muhammad Iqbal Choudhary, Karachi (PK); Sammer Yousuf, Karachi (PK); Misha Siddiqui, Karachi (PK); Madiha Mukhtar, Karachi (PK)

(*) Notice: Subject to any disclaimer, the term of this patent is extended or adjusted under 35 U.S.C. 154(b) by 224 days.

(21) Appl. No.: 15/671,191

(22) Filed: Aug. 8, 2017

(65) Prior Publication Data

US 2019/0046597 A1 Feb. 14, 2019

(51) Int. Cl.
*A61K 36/30* (2006.01)
*A61K 9/00* (2006.01)

(52) U.S. Cl.
CPC ............ *A61K 36/30* (2013.01); *A61K 9/0053* (2013.01); *A61K 2236/33* (2013.01)

(58) Field of Classification Search
None
See application file for complete search history.

(56) References Cited

PUBLICATIONS

Quaraishi, 2004, Reviews on Corrosion Inhibitor Science and Technology, vol. 3, Papers presented at the Corrosion-2004 Symposium, New Orleans, LA, United States, Mar. 28-Apr. 1, 2004 (2004), Oct. 1-Oct. 13.*
Nazim et al.,Review on Ethnobotany and Phytopharmacology of Cordia Dichotoma, 2013, J Drug Delivery, 3: 110-113.*
Lim, Assessment of Anticandidal Activity and Cytotoxicity of Root Extract from Curculigo latifolia on Pathogenic Candida, albicans, 2013, J Medical Science, 13: 193-200.*

* cited by examiner

*Primary Examiner* — Terry A McKelvey
*Assistant Examiner* — Catheryne Chen
(74) *Attorney, Agent, or Firm* — Sarfaraz K. Niazi (57) ABSTRACT

A method for treating the onset of obesity, reducing dyslipidemia and improving insulin sensitivity in mammals comprising administering a therapeutically effective amount of dried alcoholic extract of *Cordia latifolia* orally at a dose of 300 mg/kg of body weight to mammals in need for the reducing body weight and managing diabetic conditions.

2 Claims, 12 Drawing Sheets

FIG. 11: SERUM TRIGLYCERIDES LEVELS AFTER 12 WEEKS OF PREVENTIVE STUDIES ON HIGH-FAT DIET INDUCED OBESE RATS MODEL WITH *CORDIA LATIFOLIA* EXTRACT. VALUES ARE EXPRESSED AS MEAN ± SEM.

FIG. 12: SERUM HDL LEVELS AFTER 12 WEEKS OF PREVENTIVE STUDIES ON HIGH-FAT DIET INDUCED OBESE

RATS MODEL WITH *CORDIA LATIFOLIA* EXTRACT. VALUES ARE EXPRESSED AS MEAN ± SEM.

OBESITY TREATMENT

FIELD OF THE INVENTION

The present invention relates to anti-obesity use of an alcoholic extract of *Cordia latifolia* Wall. ex G. Don, wherein the treatment hardier reduces dyslipidemia and resistance to insulin.

BRIEF SUMMARY OF INVENTION

The effect of ethanolic extract of *C. latifolia* on body weights, food intake, biochemical parameters, and morphological changes in the liver and adipose tissue of high-fat diet-induced obese rat were studied in vivo.

Obese male Wistar rat models were established by feeding high-fat diets for a period of 16 weeks.

The antiobesity and anti-dyslipidemic effects of *C. latifolia* was studied at two different doses i.e. 300 mg/kg/day, and 150 mg/kg/day.

Oral application of ethanolic extract of *Cordia latifolia* at a dose of 300 mg/kg caused a significant reduction in the body weight of animals, along with ameliorated dyslipidemia and lowered serum triglyceride and VLDL (very low density lipoprotein) levels. It showed a significant positive effect in terms of weight loss, both in preventive, and in therapeutic animal model.

Oral dose of *Cordia latifolia* at a dose of 150 mg/kg does not show any significant result.

The plant extract further improved the insulin sensitivity, i.e., significantly reduced the fasting blood glucose and serum insulin levels, as well as lowered the lipase levels. Morphological observation by light microscopy displayed a dose-dependent recovery in the hepatic steatosis, caused by prolonged feeding of high-fat diets to the rats.

The application of plant extract caused no differences in the serum urea, creatinine, serum glutamic pyruvic transaminase (SGPT), aspartate aminotransferase (ALT), alkaline phosphatase (ALP), and total and direct bilirubin levels. This indicates the extract did not exert any adverse effects on renal and liver functions.

The findings dearly demonstrate the anti-obesity potential of ethanolic extract of *C. latifolia* at dose of 300 mg/kg. It also shows significant affect on leptin level. The extract significantly decreases the insulin levels. It shows no toxic effect on hepatic and renal functions on rats. It reversed the dyslipidemia in obese rats. It also positively affects other biochemical parameters, such as lowering the cholesterol, triglycerides, LDL, and VLDL levels with significant abilities of reversal of dyslipidemia and insulin resistance in vivo (high-fat diet induced obese rat models).

DETAILED DESCRIPTION OF INVENTION

Obesity is one of the major risk factors of metabolic disorders. The prevalence of obesity has dramatically increased across all genders and age groups in developed, as well as in developing countries. High-fat diet is the main reason contributing towards obesity; other factors include genetic, environmental psychological, and physical inactivity. Obesity due to chronic consumption of high-fat diets leads to the development of hypertension, hyperlipidemia, cardiovascular diseases, and insulin resistance.

Central obesity (abnormal fat distribution) and insulin resistance are the two major causative features, contributing towards the increasing rate of metabolic syndrome. Other factors, such as hormonal dysregulation, physical inactivity, pro-inflammatory state, ageing, and genetic profile have also been implicated in the development of the metabolic syndrome.

A number of rodent models have been developed for the study of the pathogenesis related to the metabolic syndrome. These studies demonstrated that high-fat diet promotes the whole-body insulin resistance and hyperglycemia. The effect of hyperglycemia and insulin resistance on liver physiology, muscle, and insulin signal transduction has also been examined by researchers. These studies indicate that the high-fat diet can be used to cause metabolic syndrome with insulin resistance, and compromised β-cell function in a rodent model. High-fat diet, fed to rodents, increases triglyceride levels in muscles followed by insulin resistance, a state equivalent to metabolic syndrome in humans. Wistar rats fed with high-fat diet are known to develop obesity, hypertension, dyslipidemia, glucose intolerance, and hyperinsulinemia; collectively called metabolic syndrome.

Most of the pharmacological approaches towards the treatment of obesity are known to possess adverse effects. The discoveries of anti-obesity drugs from plants are therefore considered as viable options.

*Cordia latifolia* Wall. ex G. Don., commonly known as lasers, belongs to the family Boraginaceae. The plant parts are reported for many medicinal properties, such as diuretic and laxative, and as a cure of diseases of lungs and spleen, cow, helminthiasis, leprosy, and skin diseases. The ripe fruits are known to contain large quantity of vitamins. For our investigation, *latifolia* extract was selected for the evaluation its anti-obesity effect in vivo, followed by detailed phytochemical and mechanistic studies.

*C. latifolia* might exert its anti-obesity action through the inhibition of intestinal absorption of dietary fat, its hypophagic activity, and its hypolipidemic activity.

Materials and Methods
Preparation of Extract and Standard Drugs.

The aerial ports of *Cordia latifolia* (10 kg) were purchased from local herbal market in Karachi (Pakistan), identified by plant taxonomist of Department of Botany, University of Karachi and a voucher specimen (G.H. No: 63223) has been deposited in the herbarium. The air dried *Cordia latifolia* (10 kg) were crushed, and soaked in ethanol (10 L). After 5 days, the plants were filtered, followed by evaporation under reduced pressures to obtain crude ethanolic extracts (450 g). The crude extracts were completely dried, under reduced pressure on Rota vapor and stored at 4° C.

The crude extracts of *C. latifolia* were suspended in distilled water before its administration to the rat models. Orlistat and Sibutramine were used as standard drugs at doses of 100 mg/kg, and 5 mg/kg, respectively (dissolved in distilled water).

Toxicity of ethanolic extracts of *Cordia latifolia* were evaluated for the measurement of $LD_{50}$ values. Animals were given oral doses, ranging between 10 mg/kg to 1000 mg/kg, and observed for 48 hrs.

Animals

Thirty male Wistar rats (210-220 g) were obtained from the animal house facility of Dr. Panjwani Center for Molecular Medicine and Drug Research (ICCBS). All animals were kept under standard conditions of temperature and humidity with a 12 h light/dark cycle, approved by the Ethical Committee of International Center for Chemical and Biological Sciences (Protocol number: 2013-0001). After one week of acclimation period, rats were randomly divided into two groups. The control group was fed with normal diet (D12450B, Research Diets, USA), whereas the other groups were fed high-fat diet (D12451, Research Diets, USA) for a period of 16-week. The compositions of the diet are given in Table—1. After 10 weeks, biochemical parameters were evaluated regularly to establish whether the model has developed the symptoms of metabolic syndrome.

Two types of diets were used in this study, i.e. low fat diet and high fat diet. These diets were acquired from Research Diets, New Brunswick, N.J., USA.

The low-fat diet contains 20% of energy as proteins, 70% of energy as carbohydrates, and 10% of energy as fat.

The high-fat diet contains 20% of energy as protein, 35% as carbohydrates, and 45% as fat (of total energy, % kcal) as shown in Table—1.

TABLE 1

Composition of the low and high-fat diets

|  | D12450B (Normal Diet) | | D12451 (High fat diet) | |
| --- | --- | --- | --- | --- |
|  | gm % | kcal % | gm % | kcal % |
| Protein | 19.2 | 20 | 24 | 20 |
| Carbohydrate | 67.3 | 70 | 41 | 35 |
| Fat | 4.3 | 10 | 24 | 45 |
| kcal/gm | 3.85 | | 4.73 | |

Extract Supplementation

After a period of 16 weeks, the group of rats on high fat diet (HF) have developed symptoms of metabolic disorders, along with insulin resistance. The HF fed rats were then sub-divided into four groups of three rats each, i.e. Group 1 (PA), Control; animals in this group received LFD and distilled water. Group 2, Pathological control (PC); animals in this group received HFD, and distilled water. Groups (PO), Animals in this group received HFD, and standard drug Orlistat (100 mg/kg/day). Group 4 (PS): Animals in this group received HFD, and standard drug Sibutramine (5 mg/kg/day). Group 5 (PC1): Animals in this group received HFD, and *C. latifolia* extract (150 mg/kg/day). Group 6 (PC2) Animals in this group received HFD, and *C. latifolia* extract (300 mg/kg/day).

Whereas for therapeutic studies the animal groups were as follow: Group 1 (TA), Control; animals in this group received LFD, and distilled water Group 2 (TC), Pathological control; animals in this group received HFD, and distilled water. Groups 3 (TO), High fat diet induced obese animals in this group received standard drug Orlistat (100 mg/kg/day). Group 4 (TS): High fat diet induced obese animals in this group received standard drug Sibutramine (5 mg/kg/day), Group 5 (TC1): High fat diet induced obese animals in this group received *C. latifolia* extract (150 mg/kg/day). Group 6 (FC2) High fat diet induced obese animals in this group received *C. latifolia* extract (300 mg/kg/day).

Food Intake and Body Weights

Body weights were recorded weekly throughout the experiment. The food intake was calculated by using following formula, as described by Ghezzi et al, 2012:

$$\text{Food intake} = \frac{\text{Daily food intake(g)}}{\sum \text{Body weight of rats in each cage(g)}}$$

Blond and Tissue Collection and Sample Preparation

For biochemical analysis after 16 weeks of experimental diet, the blood samples were taken from the tail vein alter an overnight fast, whereas after 12 weeks of treatment period, rats were subjected to anesthesia and blood was drawn by cardiac puncture. Liver and pancreas samples were prepared and stained with hematoxylin and eosin; the liver was excised and fixed in buffered formalin. The sectioned liver tissue segments were stained with hematoxylin-eosin (H-E), and observed under light microscope.

Biochemical Measurements

Blood glucose, serum insulin, total cholesterol, triglycerides, HDL, LDL, very low density lipoproteins (LDG-LP), urea, creatinine, aspartate aminotransferase (ALT), alkaline phosphatase (ALP), serum glutamic pyruvic transaminase (SGPT), and direct and total bilirubin were estimated. Fasting blood glucose levels were measured using glucometer (AccuChek Performa, Australia). Fasting insulin levels were quantified using ultra sensitive rat insulin ELISA kit (Crystal Chem. Downers Grove, USA). Insulin sensitivity was evaluated using Homeostatic Model Assessment (HOMA). Serum total cholesterol, triglycerides, HDL, LDL, VLDL, urea, creatinine, AST, ALP, SGPT, and direct and total bilirubin were analyzed using automatic analyzer (Hitachi, Roche Diagnostics 902, Tokyo, Japan).

Statistical Analysis

All data are expressed as mean±SEM. Significance was determined using the two-tailed unpaired student's t test or ANOVA. Differences>less than 0.05 were considered significant.

Results and Discussion (A) Preventive Study:

Effect of Extract Supplementation on Physical and Biochemical Parameters: Food Intake.

During preventive studies an increase in the food intake was observed by the group of animals fed on *C. latifolia* extract (PC2) at dose of 300 mg/kg, however its seems to be comparable to that of control group (PC, animal on low fat diet) Table 2.

TABLE 2

Food Intake (g/100 g) of rats during 8 weeks of preventive studies.

| Groups (Codes) | Average Food intake (g/100 g) |
|---|---|
| Control (PA) | 5.62 |
| Pathological Control (PC) | 6.23 |
| Orlistat (100 mg/kg) (PO) | 4.23 |
| Sibutramine (5 mg/kg) (PS) | 5.34 |
| *C. latifolia* (150 mg/kg) (PC1) | 5.14 |
| *C. latifolia* (300 mg/kg) (PC2) | 5.78 |

Effect of Extract Supplementation on Physical and Biochemical Parameters: Body Weight.

A significant reduction in body weight of group PC2 (fed with high diet and *C. latifolia* extract at a dosage of 300 mg/kg) was observed as compared to group PC1 (fed with high diet and *C. latifolia* extract at a dose of 150 mg/kg), and pathological control (PC) (Table 3).

TABLE 3

Average body weight (g) of rats during 8 weeks of preventive studies.

| Groups | Average body weight (g) |
|---|---|
| Control (PA) | 232 ± 0.07 |
| Pathological Control (PC) | 300 ± 0.07 |
| Orlistat (100 mg/kg) (PO) | 256 ± 0.10 |
| Sibutramine (5 mg/kg) (PS) | 251 ± 0.11 |
| *C. latifolia* (150 mg/kg) (PC1) | 284 ± 0.09 |
| *C. latifolia* (300 mg/kg) (PC2) | 259 ± 0.12 |

Biochemical Parameters:

Lipid Profile

Both groups (PC1 and PC2) taking 150 and taking 300 mg/kg of *C. latifolia* extract, respectively, showed significant decrease in serum levels of total cholesterol, triglyceride, LDL and VLDL levels as compared to the pathological control, (Table—4, FIGS. 1, 2, 3, and 4 respectively).

Figure 1:
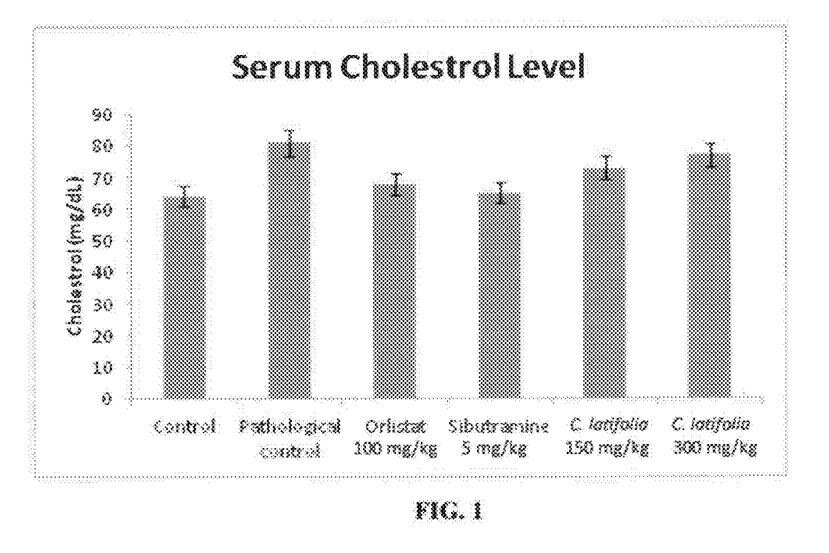
FIG. 1: Serum total cholesterol levels for 8 weeks of preventive studies of high fat diet rats with *Cordia latifolia* extract. Values are expressed as mean±SEM.
Figure 2:
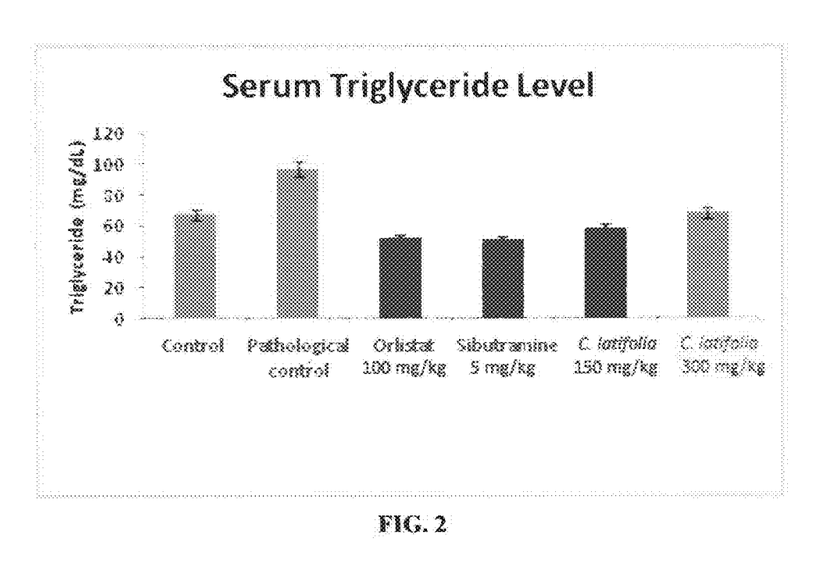
FIG. 2: Serum triglyceride levels after 8 weeks of preventive studies of high fat diet rats with *Cordia latifolia* extract. Values are expressed as mean±SEM.
Figure 3:
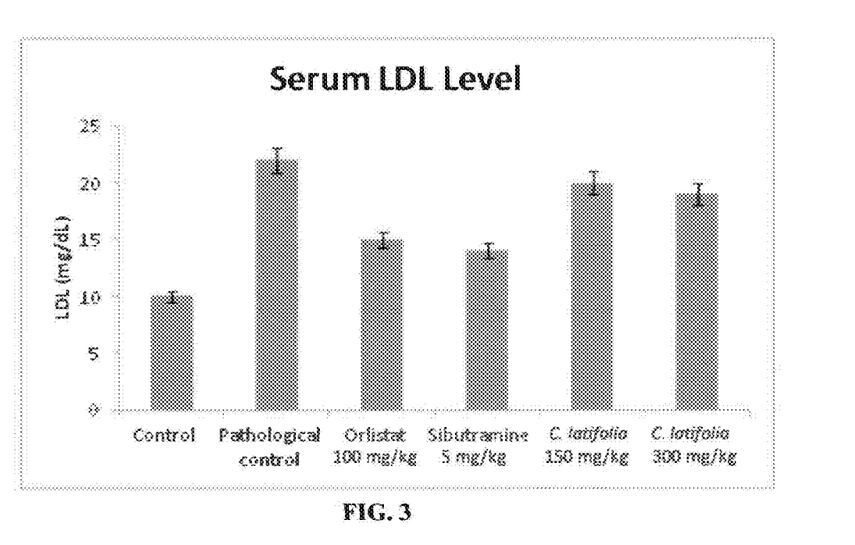
FIG. 3: Serum LDL levels after 8 weeks of preventive studies of high fat diet rats with *Cordia latifolia* extract. Values are expressed as mean±SEM.
Figure 4:
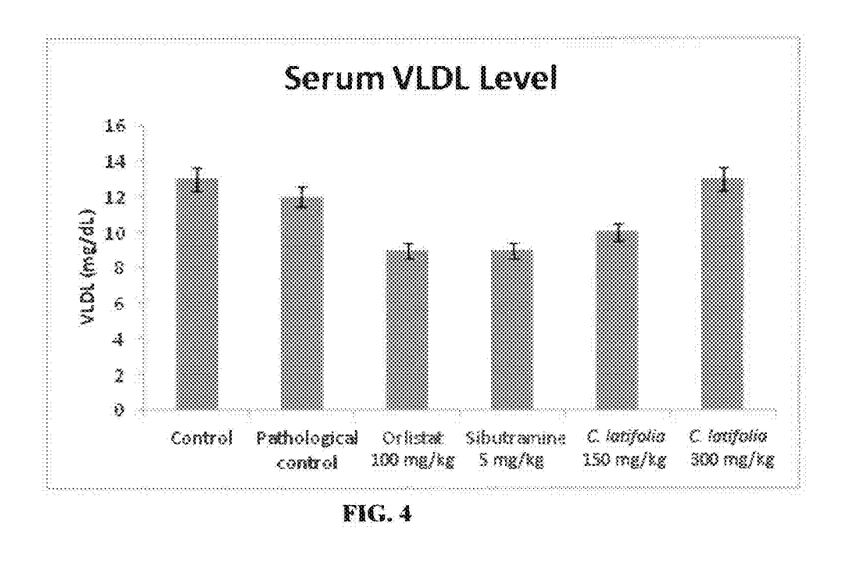
FIG. 4: Serum VLDL levels after 8 weeks of preventive studies of high fat diet rats with *Cordia latifolia* extract. Values are expressed as mean±SEM.
Figure 5:
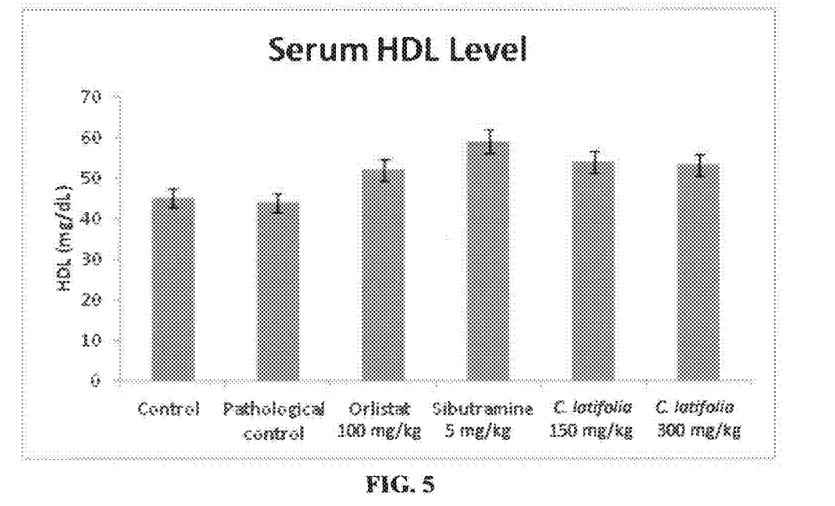
FIG. 5: Serum HDL levels alter 8 weeks of preventive studies of high fat diet with *Cordia latifolia* extract. Values are expressed as mean=SEM.

However, *Cordia latifolia* significant increase in HDL level observed both in group PC1 and PC2 as compared to pathological control (PC) further support the antiobesity effect of *C. latifolia* with ability to reverse dyslipidemia (Table—4, FIG. 5).

TABLE 4

Biochemical parameters of rats during 8 weeks of preventive studies.

| Groups | Cholestrol (mg/dL) | Triglyceride (mg/dL) | HDL (mg/dL) | LDL (mg/dL) | VLDL (mg/dL) |
|---|---|---|---|---|---|
| Control (PA) | 64 ± 2.62 | 67 ± 0.09 | 45 ± 0.56 | 10 ± 1.36 | 13 ± 2.04 |
| Pathological Control (PC) | 81 ± 0.18 | 97 ± 0.05 | 44 ± 0.31 | 22 ± 1.43 | 12 ± 3.47 |
| Orlistat (100 mg/kg) (PO) | 68 ± 3.66 | 52 ± 0.16 | 52 ± 3.04 | 15 ± 0.41 | 9 ± 0.87 |
| Sibutramine (5 mg/kg) (PS) | 65 ± 0.13 | 51 ± 0.19 | 59 ± 0.16 | 14 ± 0.68 | 9 ± 0.8 |
| *Cordia latifolia* (150 mg/kg) (PC1) | 73 ± 0.29 | 58 ± 0.32 | 54 ± 0.25 | 20 ± 0.94 | 10 ± 0.70 |
| *Cordia latifolia* (300 mg/kg) (PC2) | 77 ± 0.17 | 68 ± 0.12 | 53 ± 0.26 | 19 ± 0.38 | 13 ± 0.60 |

Fasting Blood Glucose Level

Figure 6:
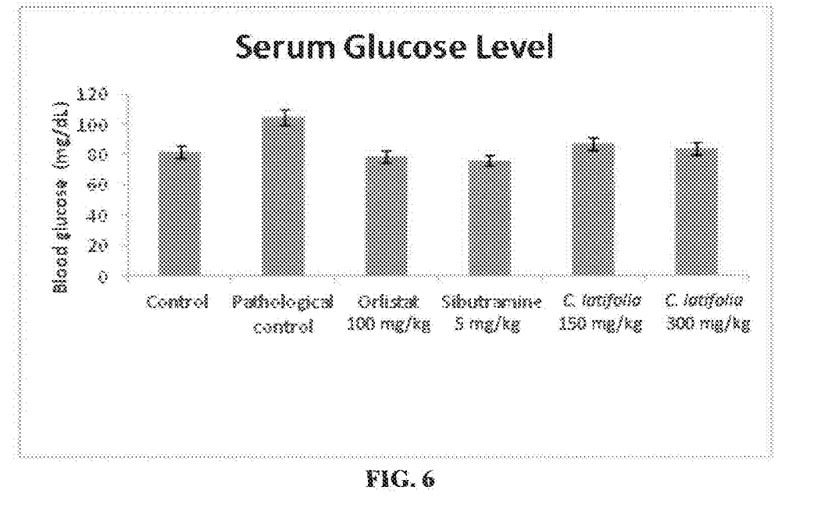
FIG. 6: Fasting blood glucose levels after 8 leeks of preventive studies of high fat diet rats model with *Cordia latifolia* extract. Values are expressed as mean±SEM.

Significant reduction in fasting blood glucose levels was seen in groups PC1 and PC2 as compared to the pathological control (PC) (Table—5, FIG. 6). The results found to be comparable to the control group (PA) further supported that *C. latifolia* extract has an ability to control the increased blood glucose level and therefore may have a potential to treat diabetes.

TABLE 5

Fasting Blood Glucose Level of Preventive Studies.

| Groups | FBG (mg/dL) |
| --- | --- |
| Control (PA) | 82 ± 1.54 |
| Pathalogical Control (PC) | 105 ± 0.20 |
| Orlistat (100 mg/kg) (PO) | 79 ± 1.04 |
| Sibutramine (5 mg/kg) (PS) | 76 ± 2.12 |
| *C. latifolia* (150 mg/kg) (PC1) | 87 ± 1.49 |
| *C. latifolia* (300 mg/kg) (PC2) | 84 ± 1.15 |

Histopathology of Liver

Figure 7:
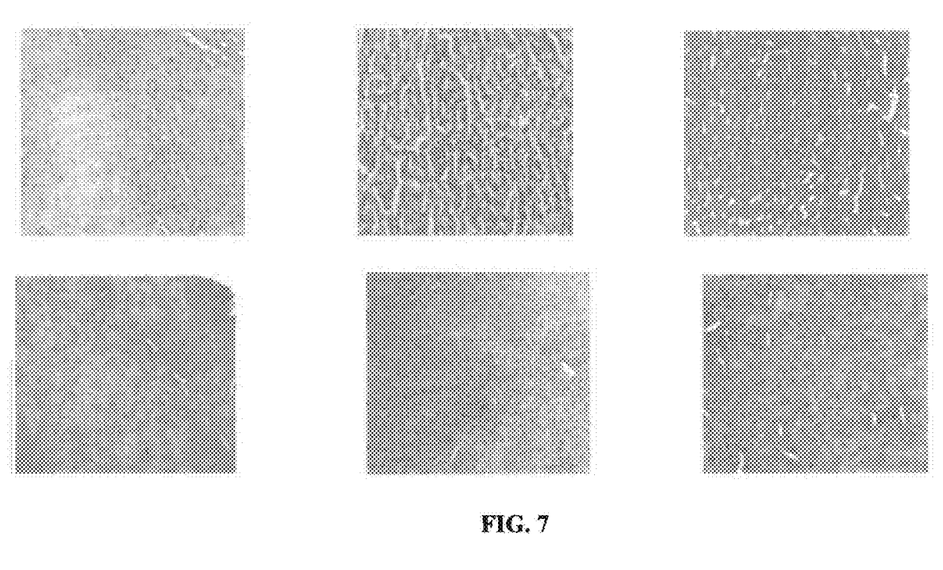
FIG. 7: Histological examination of liver tissues of high fat diet rats (preventive studies) with hematoxylin and eosin (H & E) staining; magnification 20×. Image (a) Control, (h) Pathological control, (c) Standard Orlistat (100 mg/kg), (d) Standard Sibutramine (5 mg/kg), (e) *Cordia latifolia* (150 mg/kg), and (f) *Cordia latifolia* (300 mg/kg).

Hepatic morphological changes were examined microscopically with H & E staining. An excessive fat accumulation was seen in hepatocytes of PC (pathological control group) as compared to Orlistat and Sibutramine groups. Both PC1 (treated with *Cordia latifolia* at a dose of 300 mg/kg group), and as PC2 (*Cordia latifolia* at a dose of 150 mg/kg) group showed results comparable to that control group indicating that *Cordia latifolia*, also decreasing the accumulation of fats in liver. With the help of liver cell images, it was conclude that severe steatosis occurs only in pathological control group, as shown in FIG. 7.

(B) Therapeutic Study:

In therapeutic study, we investigated the capacity of *C. latifolia* to reduced weight of high fat diet induced obese rats sod to improve the key biochemical parameters in metabolic disorders. The ability to reduce the gained weight by high fat diet induced obese rats was observed at two different doses of *C. latifolia* i.e. 150 mg/kg and 300 mg/kg.

Establishment of Obese Rat Model

Food Intake and Body Weight

Obesity was induced in normal rats by giving them a high-fat diet for 16 weeks. When we compared the food intake of both groups (i.e. low fat diet and high-fat diet), we observed that there was no significant difference in the food intake of rats as shown in Table—7.

TABLE 6

Daily food intake (mean ± SEM) by rats.

| Groups | Food intake (gm/100 gm) |
| --- | --- |
| Low-fat diet group (LFD) | 4.69 ± 0.19 |
| High-fat diet (HFD) | 3.82 ± 0.13 |

Figure 8:
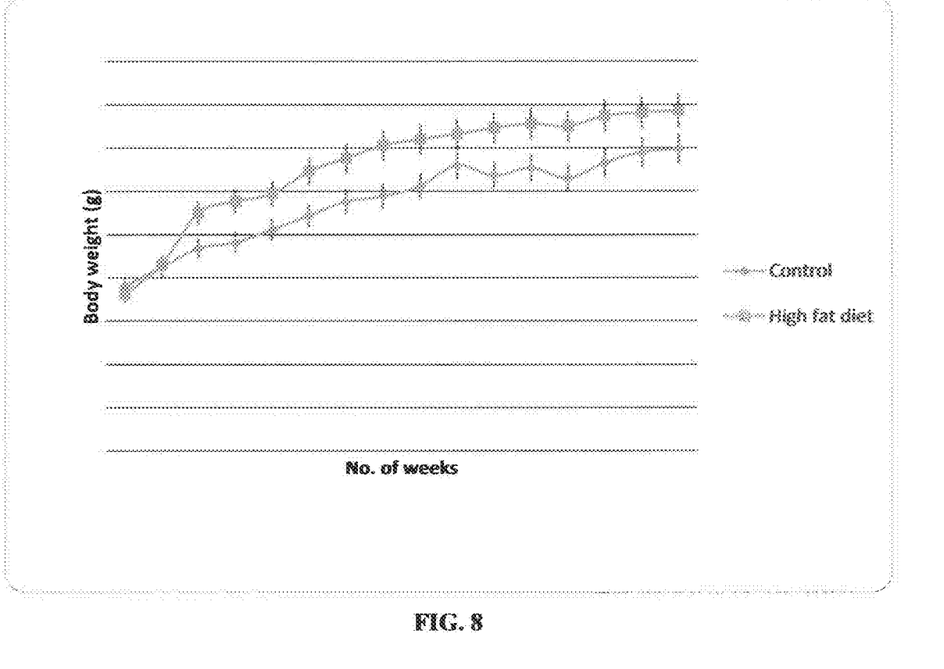
FIG. 8: Change in body weights of control and high fat diet supplemented rats during 16 weeks of experimental diet.

A clear change in body weight we seen by providing a high-fat diet for 16 weeks to animals. We observed a gradual increase in body weight as compared to the low-fat diet group as shown in FIG. 8.

Lipid Profile

The successful establishment of the animal model was confirmed based on biochemical parameters, such as fasting blood glucose, serum cholestrol, triglyceride, VLDL, HDL and LDL levels.

Results showed that total cholesterol, triglyceride, LDL, and VLDL levels in serum significantly increased in high-fat diet group, as compared to the control group. The HDL level was decreased in high-fat diet rats, as compared to the control rats group. These changes indicated a condition of dyslipidemia in rats fed with high-fat diet. The fasting blood glucose level was significantly increased in high-fat diet group, as compared to the control group as shown in Table—7.

TABLE 7

Effect of normal diet and high-fat diet on the serum glucose and serum lipid profile after 16 weeks of experimental diet to rats.

| Serum parameters | Low fat diet group (LFD) | High fat diet group (HFD) |
| --- | --- | --- |
| FBG (mg/dL) | 83 ± 0.47 | 92.5 ± 3.76 |
| Cholesterol (mg/dL) | 79.4 ± 7.26 | 80.33 ± 3.41 |
| Triglyceride (mg/dL) | 168 ± 4.61 | 204 ± 0.03 |
| HDL (mg/dL) | 51.16 ± 2.70 | 37.6 ± 1.94 |
| LDL (mg/dL) | 25 ± 2.7 | 27.25 ± 3.11 |
| VLDL (mg/dL) | 10.5 ± 2.04 | 33.4 ± 8.02 |

Effect of Extract Supplementation on Physical and Biochemical Parameters: Food Intake.

Obese rats were treated with *Cordia latifolia* extracts, at two different doses i.e. 150 mg/kg and 300 mg/kg of body weight fix 12 weeks. During these 12 weeks they were also fed HFD. Results showed a decrease in the average food intake of rats in the Orlistat (TO), Sibutramine (TS), and *Cordia latifolia* extracts (TC1, and TC2) treated groups, as shown in Table—8.

TABLE 8

Average food intake of rats during 12 weeks of treatment period.

| Groups | Average Food Intake (g/100 g) |
| --- | --- |
| Control (TA) | 3.40 |
| Pathological control (TP) | 5.68 |
| Orlistat (100 mg/kg) (TO) | 3.18 |
| Sibutramine (5 mg/kg) (TS) | 4.20 |
| *Cordia latifolia* (150 mg/kg) (TC1) | 3.80 |
| *Cordia latifolia* (300 mg/kg) (TC2) | 3.88 |

Effect of Extract Supplementation on Physical and Biochemical Parameters: Body Weights.

Figure 9:
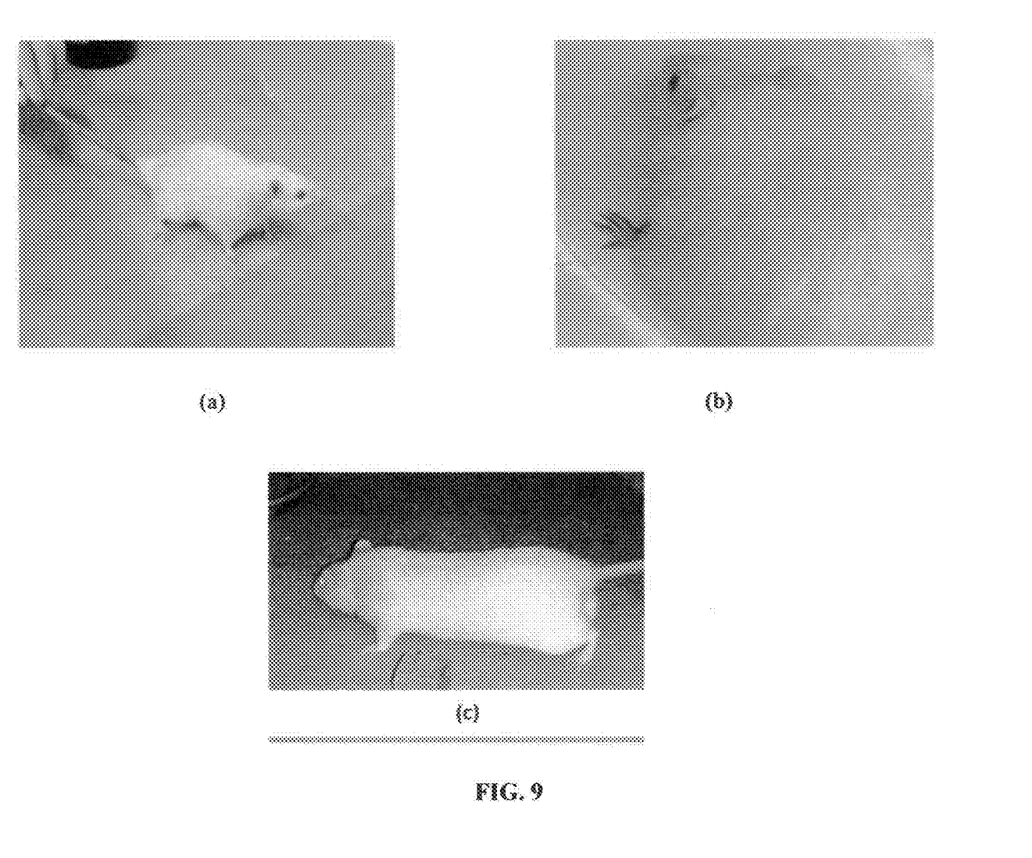
FIG. 9: Images (a) and (b) represent the marked difference of weight gain of rats on normal and high-fat diet, respectively. Image (c) represents the anti-obesity effect of *Cordia latifolia* at a dose of 300 mg/kg.
Figure 10:
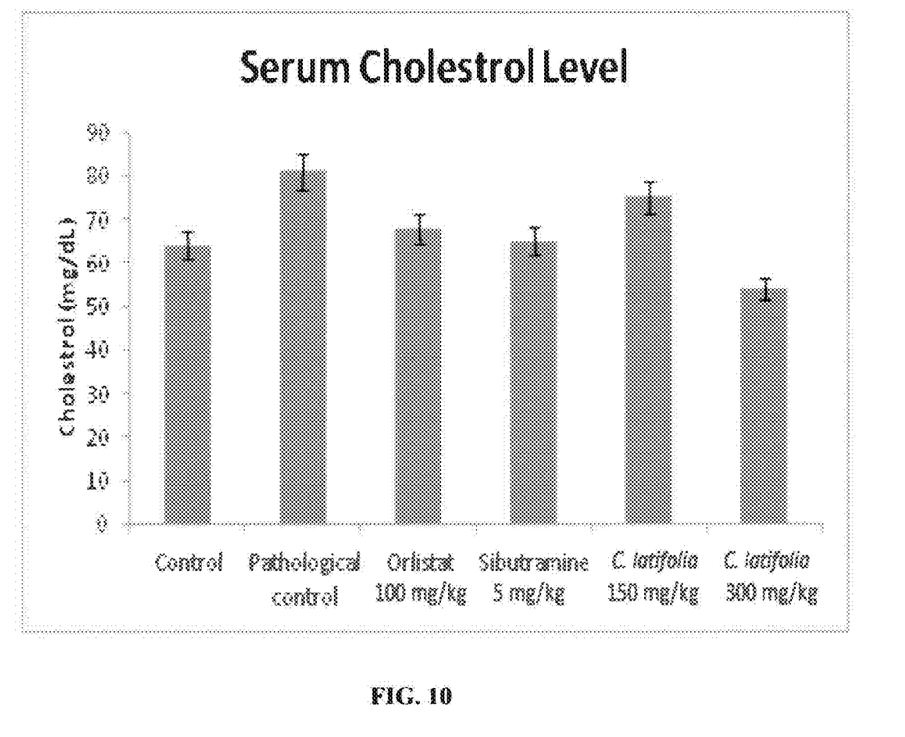
FIG. 10: Serum total cholesterol levels after 12 weeks of therapeutic studies on high-fat diet induced obese rats model with *Cordia latifolia* extract. Values are expressed as mean±SEM.
Figure 11:
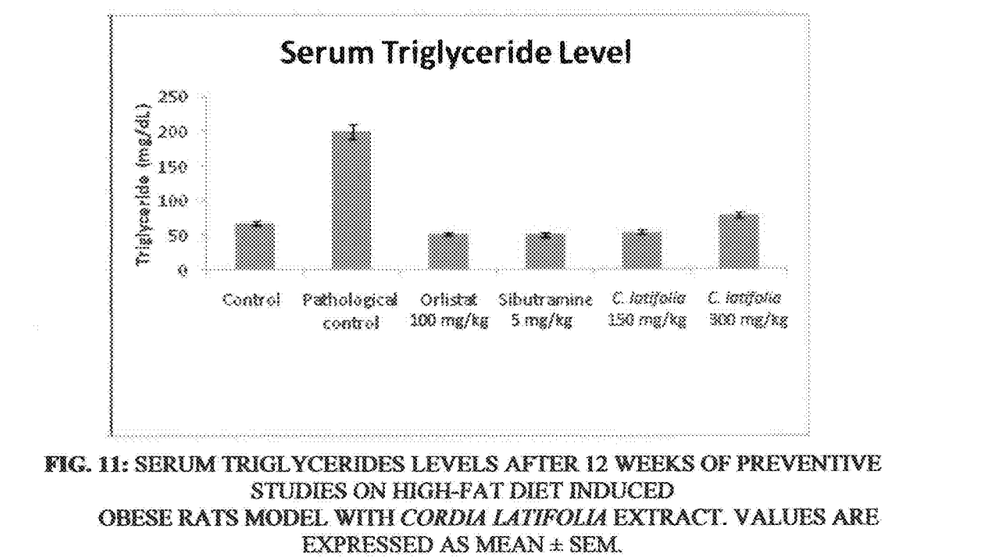
FIG. 11: Serum triglycerides levels after 12 weeks of therapeutic studies on high-fat diet induced obese rats model with *Cordia latifolia* extract. Values are expressed as mean±SEM.
Figure 12:
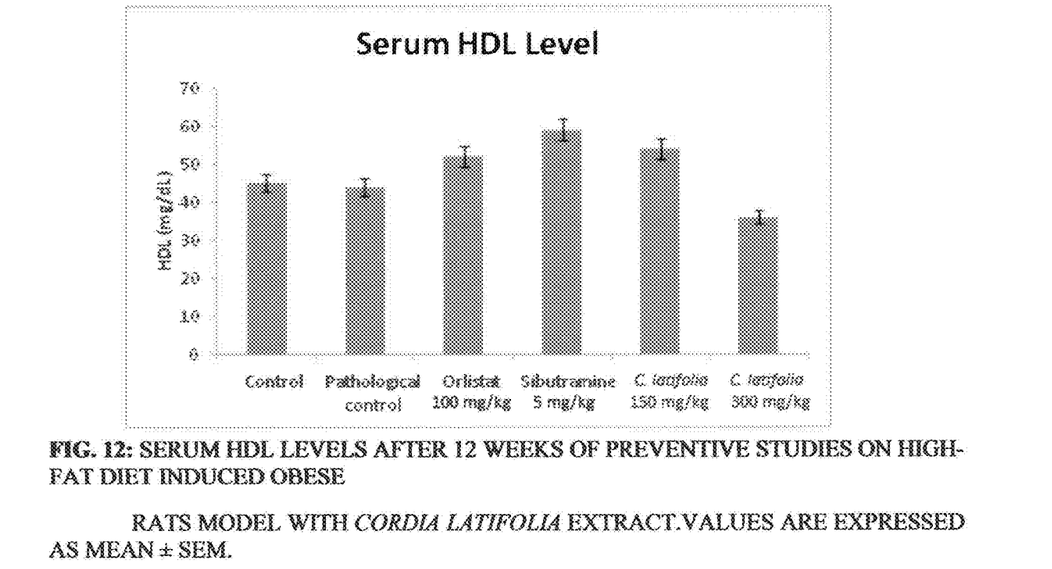
FIG. 12: Serum HDL levels-after 12 weeks of therapeutic studies on high-fat diet induced obese rats model with *Cordia latifolia* extract. Values are expressed as mean±SEM.
Figure 13:
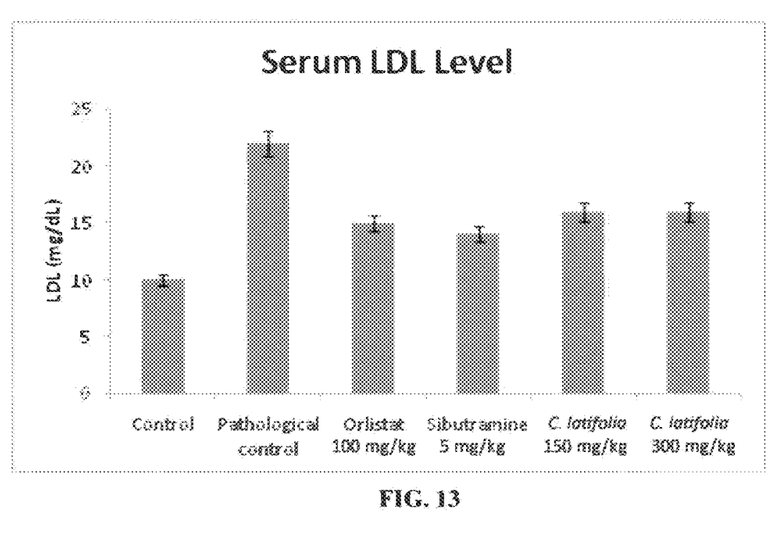
FIG. 13: Serum LDL levels after 12 weeks of therapeutic studies on high-fat diet induced obese rats model with *Cordia latifolia* extract. Values are expressed as mean±SEM.
Figure 14:
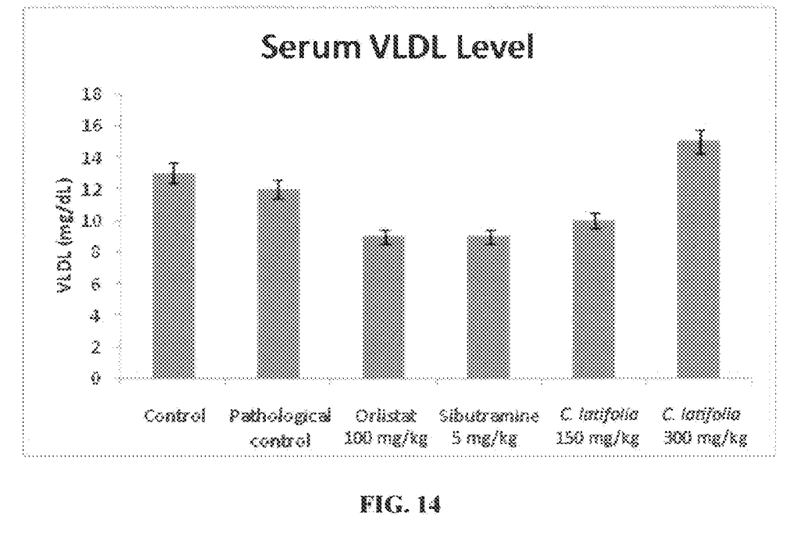
FIG. 14: Serum VLDL levels after 12 weeks of therapeutic studies on high-fat diet induced obese rats model with *Cordia latifolia* extract. Values are expressed as mean±SEM.

During 12 weeks of treatment period, groups TC1 and TC2 having *C. latifolia* extract at a dose of 150 and 300 mg/kg respectively showed significant weight loss, as compared to compared to TP (pathological control). Results are summarized in Table—9 and depicted in FIG. 9.

TABLE 9

Average Body weight of rats during 12 weeks of treatment period.

| Groups | Average Body Weight (g) |
| --- | --- |
| Control (TA) | 376 ± 2.16 |
| Pathological control (TP) | 431 ± 2.68 |
| Orlistat (100 mg/kg) (TO) | 356 ± 4.63 |
| Sibutramine (5 mg/kg) (TS) | 361 ± 6.43 |
| *Cordia latifolia* (150 mg/kg) (TC1) | 382 ± 5.49 |
| *Cordia latifolia* (300 mg/kg) (TC2) | 377 ± 4.10 |

Lipid Profile

The group TC2 (*Cordia latifolia* at dose of 300 mg/kg) showed a reduction in total serum cholesterol, triglyceride, HDL, LDL and VLDL level in comparison to TP (pathological control). Whereas, there was a significant improvement in HDL level was observed for TC1 group (*Cordia latifolia* at dose of 150 mg/kg) when compared with the TP as shown in Table—10 and depicted in FIGS. 10, 11, 12, 13 and 14.

These results clearly indicated a condition of reversal of dyslipidemia in rats fed with high-fat diet, as shown in Table—10, and depicted in FIGS. 10, 11, 12, 13, and 14,

TABLE 10

Biochemical parameter after 12 weeks of treatment in serum of normal and obese experimental rats.

| Groups | Cholesterol (mg/dL) | Triglycerides (mg/dL) | HDL (mg/dL) | LDL (mg/dL) | VLDL (mg/dL) |
| --- | --- | --- | --- | --- | --- |
| Control (TA) | 64 ± 2.62 | 67 ± 0.09 | 45 ± 0.56 | 10 ± 1.36 | 13 ± 2.04 |
| Pathological control (TP) | 81 ± 0.18 | 200 ± 0.05 | 44 ± 0.31 | 22 ± 1.43 | 12 ± 3.47 |
| Orlistat (100 mg/kg) (TO) | 68 ± 3.66 | 52 ± 0.16 | 52 ± 3.04 | 15 ± 0.41 | 9 ± 0.87 |
| Sibutramine (5 mg/kg) (TS) | 65 ± 0.13 | 51 ± 0.19 | 59 ± 0.16 | 14 ± 0.68 | 9 ± 0.8 |
| Cordia latifolia (150 mg/kg) (TC1) | 75 ± 0.89 | 55 ± 0.27 | 54 ± 0.56 | 16 ± 1.08 | 10 ± 0.58 |
| Cordia latifolia (300 mg/kg) (TC2) | 54 ± 0.98 | 79 ± 0.17 | 36 ± 0.89 | 16 ± 1.07 | 15 ± 0.87 |

Fasting Blood Glucose Levels

Figure 15:
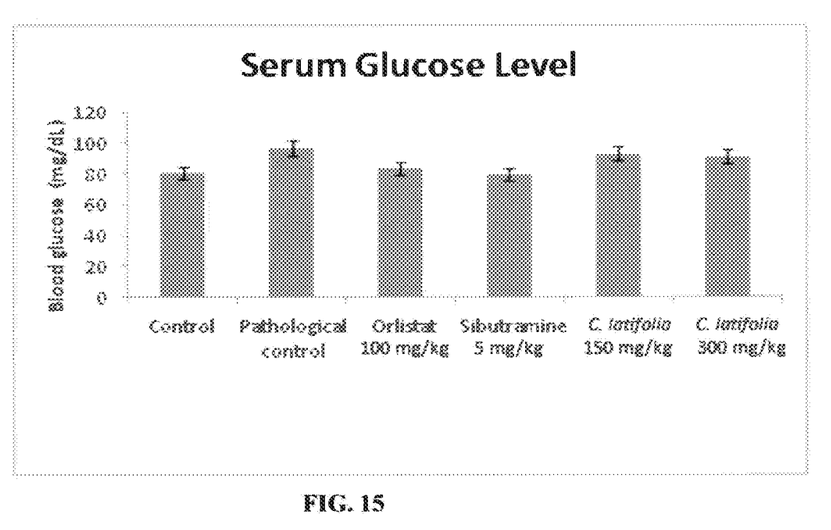
FIG. 15: Fasting blood glucose levels after 12 weeks of therapeutic studies on high-fat diet induced obese rats model with *Cordia latifolia* extract. Values are expressed as mean±SEM.

Group TC1 (*Cordia latifolia* extract at dose 300 mg/kg) as well as TO and TC also reduced the fasting blood glucose levels when compared with the pathological control group, as shown in Table—11 and depicted in FIG. 15.

TABLE 11

Fasting blood glucose level after 12 weeks of treatment period in the serum of normal and obese experimental rats.

| Groups | FBG (mg/dL) |
| --- | --- |
| Control (TA) | 81 ± 0.12 |
| Pathological control (TP) | 97 ± 0.14 |
| Orlistat (100 mg/kg) (TO) | 84 ± 0.17 |
| Sibutramine (5 mg/kg) (TS) | 80 ± 0.12 |
| Cordia latifolia (150 mg/kg) (TC1) | 93 ± 0.22 |
| Cordia latifolia (300 mg/kg) (TC2) | 82 ± 0.27 |

Figure 16:
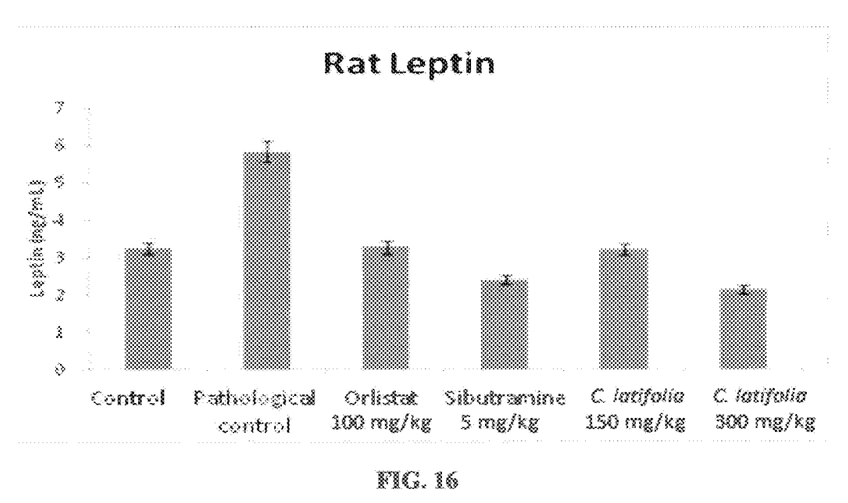
FIG. 16: Serum leptin levels after 12 weeks of therapeutic studies on high-fat diet induced obese rats model with *Cordia latifolia* extract. Values are expressed as mean±SEM.

Leptin Assessment:

*Cordia latifolia* at a dose 300 mg/kg (TC2) of body weight significantly reduced the leptin levels, when compared with the TP (pathological control), and standards supplemented groups (TO and TS) as shown in Table 12 and depicted in FIG. 16.

TABLE 12

Serum leptin dose after 12 weeks of treatment period to normal and obese experimental rats.

| Groups | Rat Leptin (mg/mL) |
| --- | --- |
| Control (TA) | 3.24 ± 0.12 |
| Pathological control (TP) | 5.82 ± 1.39 |
| Orlistat (100 mg/kg) (TO) | 3.26 ± 0.42 |
| Sibutramine (5 mg/kg) (TS) | 2.39 ± 1.11 |
| Cordia latifolia (150 mg/kg) (TC1) | 3.21 ± 0.20 |
| Cordia latifolia (300 mg/kg) (TC2) | 2.12 ± 0.13 |

Insulin Resistance Assessment.

Figure 17:
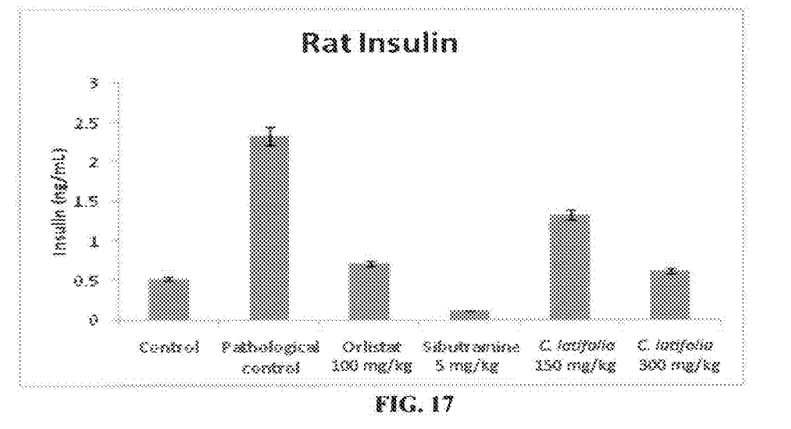
FIG. 17: Serum insulin levels after 12 weeks of therapeutic studies on high fat diet induced obese rats model with *Cordia latifolia* extract. Values are expressed as mean±SEM

*Cordia latifolia* extract both at doses of 150 mg/kg and 300 mg/kg body weight of animal rats significantly decreased the serum insulin level, Group TC1 showed results comparable to TA and TO groups and clearly indicate the insulin resistance reversal ability of *Cordia latifolia* extract at dose of 300 mg/kg (Table—13, FIG. 17).

TABLE 13

Serum insulin estimation after 12 weeks of treatment period.

| Groups | Fasting Insulin (mg/ml) |
| --- | --- |
| Control (TA) | 0.52 ± 0.14 |
| Pathological control (TP) | 2.32 ± 0.92 |
| Orlistat (100 mg/kg) (TO) | 0.71 ± 0.32 |
| Sibutramine (5 mg/kg) (TS) | 0.12 ± 0.31 |
| Cordia latifolia (150 mg/kg) (TC1) | 1.33 ± 0.23 |
| Cordia latifolia (300 mg/kg) (TC2) | 0.62 ± 0.16 |

Evaluation of Renal and Liver Toxicity of *Cordia latifolia* Extract:

A slight reduction in the level of urea and creatinine was seen in TC1 and TC2 groups, as compared to TA (control group). The result indicated that *Cordia latifolia* did not, cause any adverse effects on renal functions.

TABLE 14

Renal toxicity assessment after 12 weeks of treatment period to normal and obese experimental rats.

| Groups | Urea (mg/dL) | Creatinine (mg/dL) |
| --- | --- | --- |
| Control (TA) | 21 ± 1.87 | 0.46 ± 0.01 |
| Pathological control (TP) | 38 ± 1.42 | 0.47 ± 0.02 |
| Orlistat (100 mg/kg) (TO) | 30 ± 1.63 | 0.41 ± 0.01 |
| Sibutramine (5 mg/kg) (TS) | 31 ± 2.42 | 0.49 ± 0.02 |
| Cordia latifolia (150 mg/kg) (TC1) | 16 ± 3.31 | 0.31 ± 0.02 |
| Cordia latifolia (300 mg/kg) (TC2) | 18 ± 1.56 | 0.36 ± 0.03 |

The ALP and ALT levels of *Cordia latifolia* supplemented groups, (TC1 and TC2) were in a normal range and comparable to that of TO and TS groups. The elevated ALP levels indicated hepatotoxicity in obese rats (pathological control) due to the accumulation of fat in liver cells.

TABLE 15

Liver toxicity assessment after 12 weeks of treatment period in normal and obese experimental rats.

| Groups | Total bilirubin (mg/dL) | Direct bilirubin (mg/dL) | SGPT (U/L) | ALP (U/L) | ALT (U/L) |
|---|---|---|---|---|---|
| Control (TA) | 0.11 ± 0.004 | 0.05 ± 0.008 | 32 ± 1.17 | 85 ± 0.12 | 108 ± 0.07 |
| Pathological control (TP) | 0.17 ± 0.008 | 0.07 ± 0.004 | 42 ± 5.85 | 240 ± 0.09 | 155 ± 0.08 |
| Orlistat (100 mg/kg) (TO) | 0.13 ± 0.004 | 0.06 ± 0.008 | 48 ± 6 | 129 ± 0.19 | 108 ± 1.44 |
| Sibutramine (5 mg/kg) (TS) | 0.15 ± 0.01 | 0.03 ± 0.004 | 38 ± 3.34 | 116 ± 0.14 | 85 ± 0.009 |
| Cordia latifolia (150 mg/kg) (TC1) | 0.16 ± 0.02 | 0.07 ± 0.01 | 46 ± 3.56 | 116 ± 0.13 | 106 ± 0.12 |
| Cordia latifolia (300 mg/kg) (TC2) | 0.15 ± 0.01 | 0.06 ± 0.01 | 46 ± 2.76 | 101 ± 0.30 | 106 ± 0.14 |

Figure 18:
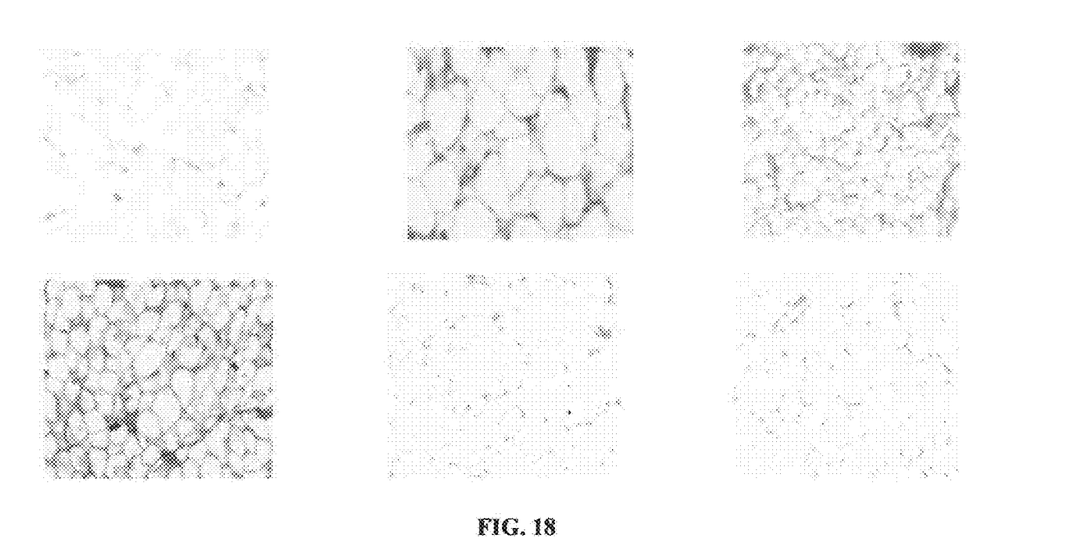
FIG. 18: Histological examination of adipose tissues (therapeutic studies group) with hematoxylin and eosin (H & E) stainings; magnification 20×. Image (a) Control, (b) Pathological Control, (c) Standard Orlistat (100 mg/kg), (d) Standard Sibutramine (5 mg/kg), (e) *Cordia latifolia* (150 mg/kg), and (f) *Cordia latifolia* (300 mg/kg).
Figure 19:
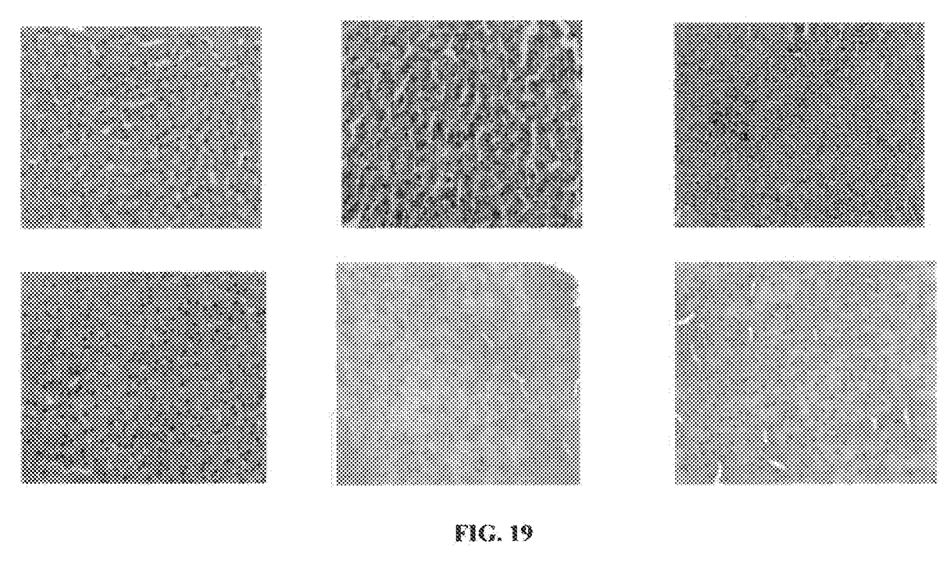
FIG. 19: Histological examination of liver tissues with hematoxylin and eosin (H & E) staining; magnification 20×. Image (a) Control, (b) Pathological control, (c) Standard Orlistat (100 mg/kg), (d) Standard Sibutramine (5 mg/kg), (e) *Cordia latifolia* (150 mg/kg), and (f) *Cordia latifolia* (300 mg/kg).

Histological Examination of Adipose Tissue:

Microscopically, the cells of adipose tissues of groups TC1 and TC2 treated with *Cordia latifolia* at a dose of 150 and 300 mg/kg of body weight, respectively were decrease in size to the normal level (FIG. 18c and FIG. 18f), as observed through H & F staining. An excessive fat accumulation in adipocytes of pathological control group was observed clearly (FIG. 18b).

Histological Examination of Liver:

Hepatic morphological changes were examined microscopically with H & F staining. An excessive fat accumulation was seen in hepatocytes of TC (pathological control group) as compared to orlistat and Sibutramine groups. Both TC1 (treated with *Cordia latifolia* at a dose of 300 mg/kg group), and as TC2 (*Cordia latifolia* at a dose of 150 mg/kg) group showed results comparable to that control group, is that *Cordia latifolia* also decreasing the accumulation of fats in liver. With the help of liver cell images, it was concluded that severe steatosis occurs only in pathological control group, as shown in FIG. 7.

What is claimed:

1. A method for treating onset of obesity in mammals comprising administering a therapeutically effective amount of dried alcoholic extract of *Cordia latifolia* orally at a dose of 300 mg/kg of body weight to mammals in need for the treatment.

2. The method of claim 1, wherein the treatment further results in increased insulin sensitivity, lower fasting blood glucose levels, reduced dyslipidemia, serum triglyceride, and very low density lipoprotein (VLDL).

* * * * *